United States Patent
Bradford et al.

(10) Patent No.: US 8,609,701 B2
(45) Date of Patent: *Dec. 17, 2013

(54) PIRFENIDONE TREATMENT FOR PATIENTS WITH ATYPICAL LIVER FUNCTION

(75) Inventors: Williamson Ziegler Bradford, Ross, CA (US); Javier Szwarcberg, San Francisco, CA (US)

(73) Assignee: Intermune, Inc., Brisbane, CA (US)

( * ) Notice: Subject to any disclaimer, the term of this patent is extended or adjusted under 35 U.S.C. 154(b) by 122 days.

This patent is subject to a terminal disclaimer.

(21) Appl. No.: 13/128,569

(22) PCT Filed: Nov. 9, 2009

(86) PCT No.: PCT/US2009/063702
§ 371 (c)(1),
(2), (4) Date: Jul. 13, 2011

(87) PCT Pub. No.: WO2010/054294
PCT Pub. Date: May 14, 2010

(65) Prior Publication Data
US 2011/0263656 A1    Oct. 27, 2011

Related U.S. Application Data

(63) Continuation of application No. 12/553,292, filed on Sep. 3, 2009, now Pat. No. 7,635,707, which is a continuation-in-part of application No. 12/488,228, filed on Jun. 19, 2009, now abandoned, which is a continuation of application No. 12/428,393, filed on Apr. 22, 2009, now Pat. No. 7,566,729.

(60) Provisional application No. 61/113,107, filed on Nov. 10, 2008, provisional application No. 61/228,943, filed on Jul. 27, 2009.

(51) Int. Cl.
*A01N 43/40* (2006.01)
*A61K 31/44* (2006.01)

(52) U.S. Cl.
USPC ............ 514/345; 514/350; 546/261; 546/262

(58) Field of Classification Search
None
See application file for complete search history.

(56) References Cited

U.S. PATENT DOCUMENTS

| | | | |
|---|---|---|---|
| 5,310,562 A | 5/1994 | Margolin | |
| 5,518,729 A | 5/1996 | Margolin | |
| 5,716,632 A | 2/1998 | Margolin | |
| 6,294,350 B1 | 9/2001 | Peterson | |
| 6,956,044 B1 * | 10/2005 | Margolin | 514/315 |
| 7,247,711 B2 | 7/2007 | Benson et al. | |
| 7,407,973 B2 | 8/2008 | Ozes et al. | |
| 7,605,173 B2 | 10/2009 | Seth | |
| 7,638,480 B2 | 12/2009 | Power et al. | |
| 7,696,236 B2 | 4/2010 | Bradford | |
| 7,728,013 B2 | 6/2010 | Blatt et al. | |
| 7,807,471 B2 | 10/2010 | Benson et al. | |
| 7,825,133 B2 | 11/2010 | Yi | |
| 1,000,828 A1 | 1/2011 | Blatt et al. | |
| 7,988,994 B2 * | 8/2011 | Radhakrishnan et al. | 424/452 |
| 2004/0157772 A1 | 8/2004 | Kirk | |
| 2005/0049206 A1 | 3/2005 | Gong et al. | |
| 2005/0142074 A1 * | 6/2005 | Pushpangadan et al. | 424/48 |
| 2005/0232923 A1 | 10/2005 | Yan et al. | |
| 2005/0266005 A1 | 12/2005 | Heavner et al. | |
| 2006/0105995 A1 | 5/2006 | Fujimoto et al. | |
| 2006/0110358 A1 | 5/2006 | Hsu | |
| 2006/0246070 A1 | 11/2006 | Heavner et al. | |
| 2006/0258706 A1 | 11/2006 | Saindane et al. | |
| 2007/0009518 A1 | 1/2007 | Novobrantseva et al. | |
| 2007/0053877 A1 | 3/2007 | Crager et al. | |
| 2007/0054842 A1 | 3/2007 | Blatt et al. | |
| 2007/0072181 A1 | 3/2007 | Blatt | |
| 2007/0092488 A1 | 4/2007 | Strieter et al. | |
| 2007/0117841 A1 | 5/2007 | Ozes et al. | |
| 2007/0172446 A1 | 7/2007 | Blatt | |
| 2007/0203202 A1 | 8/2007 | Robinson et al. | |
| 2007/0203203 A1 | 8/2007 | Tao et al. | |
| 2008/0003635 A1 | 1/2008 | Ozes et al. | |
| 2008/0019942 A1 | 1/2008 | Seiwert et al. | |
| 2008/0025986 A1 | 1/2008 | Ozes et al. | |

(Continued)

FOREIGN PATENT DOCUMENTS

| | | |
|---|---|---|
| AU | 2007201663 | 10/2008 |
| CA | 2583716 | 10/2008 |

(Continued)

OTHER PUBLICATIONS

Salazar-Montes et al., Potent antioxidant role of pirfenidone in experimental cirrhosis. *Eur. J. of Pharmacol.* 595: 69-77 (2008).

(Continued)

*Primary Examiner* — Jeffrey S. Lundgren
*Assistant Examiner* — Meghan Finn
(74) *Attorney, Agent, or Firm* — Marshall, Gerstein & Borun LLP; John Bendrick; Carolyn Tang

(57) ABSTRACT

Methods are provided for administering pirfenidone to a patient that has exhibited abnormal biomarkers of liver function in response to pirfenidone administration. The methods include administering to a patient pirfenidone at doses lower than the full target dosage for a time period, followed by administering to the patient pirfenidone at the full target dosage. The methods also include administering pirfenidone at the full target dose with no reduction and administering permanently reduced doses of pirfenidone.

19 Claims, No Drawings

(56) References Cited

U.S. PATENT DOCUMENTS

| | | | |
|---|---|---|---|
| 2008/0194644 A1 | 8/2008 | Bradford |
| 2008/0260650 A1 | 10/2008 | Tawakol et al. |
| 2008/0260820 A1 | 10/2008 | Borrelly et al. |
| 2008/0287508 A1 | 11/2008 | Robinson et al. |
| 2009/0110633 A1 | 4/2009 | Sengupta et al. |
| 2009/0131312 A1 | 5/2009 | Blatt et al. |
| 2009/0136512 A1 | 5/2009 | Bugelski et al. |
| 2009/0170804 A1 | 7/2009 | Phillips et al. |
| 2009/0191265 A1 | 7/2009 | Radhakrishnan et al. |
| 2009/0197923 A1 | 8/2009 | Bradford |
| 2009/0258911 A1 | 10/2009 | Tao et al. |
| 2009/0318455 A1 | 12/2009 | Kossen et al. |
| 2010/0022568 A1 | 1/2010 | Clozel et al. |
| 2010/0111898 A1 | 5/2010 | Pelura |
| 2010/0152250 A1 | 6/2010 | Radhakrishnan et al. |
| 2010/0240704 A1 | 9/2010 | Blatt et al. |
| 2010/0260749 A1 | 10/2010 | Kinch et al. |
| 2010/0272822 A1 | 10/2010 | Sengupta et al. |
| 2010/0324097 A1 | 12/2010 | Bradford |
| 2011/0034495 A1 | 2/2011 | Seiwert et al. |

FOREIGN PATENT DOCUMENTS

| | | |
|---|---|---|
| EP | 1138329 A2 | 10/2001 |
| WO | WO-2005067963 | 7/2005 |
| WO | WO-2005110478 | 11/2005 |
| WO | WO-2006105538 | 10/2006 |
| WO | WO-2007038264 | 4/2007 |

OTHER PUBLICATIONS

Azuma et al., Double-blind, placebo-controlled trial of pirfenidone in patients with idiopathic pulmonary fibrosis. *Am. J. Resp. Crit. Care Med.* 171: 1040-7 (2005).

García et al., Pirfenidone effectively reverses experimental liver fibrosis. *J. of Hepatol.* 37: 797-805 (2002).

Lasky, Pirfenidone. *IDrugs* 7(2): 166-72 (2004).

Dosanjh, Pirfenidone: a novel potential therapeutic agent in the management of chronic allograft rejection. *Transplant. Proc.* 39: 2153-6 (2007).

Shi et al., Single- and multiple-dose pharmacokinetics of pirfenidone, an antifibrotic agent, in healthy Chinese volunteers. *J. Clin. Pharmacol.* 47: 1268-1276 (2007).

Angulo et al., Pirfenidone in the treatment of primary sclerosing cholangitis. *Dig. Dis. Sci.* 47(1): 157-61 (2002).

Senior, Monitoring for hepatotoxicity: what is the predictive value of liver "function" tests? *Clin. Phamacol. Ther.* 85(3): 331-334 (2009).

Pirespa® package insert, Shionogi & Co., Ltd. Prepared in Oct. 2008 ($1^{st}$ version).

Azemar et al., Regression of cutaneous tumor lesions in patients intratumorally injected with a recombinant single-chain antibody-toxin targeted to ErbB2/HER2. *Breast Cancer Res. Treat.* 82: 155-164 (2003).

de Boer et al., Myelotoxicity and hepatotoxicity during azathioprine therapy. *Neatherlands J. Med.* 63(11): 444-446 (2005).

FDA, New Warning for Strattera, Dec. 17, 2004.

FDA, Questions and Answers on Ketek (telithromycin), Feb. 12, 2007 (available at http://www.fda.gov/Drugs/DrugSafety/PostmarketDrugSafetyInformationforPatientsandProviders/ucm107826.htm, last visited Jun. 5, 2009).

Hammoud et al., Poor tolerability to high dose PEG interferon and ribavirin in HIV/HCV coinfected patients; Initial results from a randomized multicenter trial. *Hepatol.* 38(4): Suppl.1 327A (2003).

Kai et al., Imatinib mesylate induced fatal hepatitis B virus (HBV) reactivation in a patient with CML. *Blood* 104: Abstract 4677 (2004).

Ladas et al., Milk thistle is associated with reductions in liver function test (LFTs) in children undergoing therapy for acute lymphoblastic leukemia (ALL). *Blood* 108: Abstract 1882 (2006).

Parafon Forte® DSC (chlorzoxazone) package insert, Ortho-McNeil Pharmaceutical, Inc. Revised Aug. 2000.

Ridruejo et al., Imatinib-induced fatal acute liver failure. *World J. Gastroenterol.* 13(48): 6608-6611 (2007).

Scherpbier et al., Once-daily highly active antiretroviral therapy for HIV-infected children: Safety and efficacy of an efavirenz-containing regimen. *Pediatrics* 119: e705-e715 (2007).

Tostmann et al., Antituberculosis drug-induced hepatotoxicity is unexpectedly low in HIV-infected pulmonary tuberculosis patients in Malawi. *Trop. Med. International Health.* 12(7): 852-855 (2007).

Tracleer® Bosentan Tablets package insert, Actelion Pharmaceuticals US, Inc. Prepared Mar. 2009.

Yoshimoto et al., Transient liver injury caused by gefitinib. *J. Japanese Respiratory Soc.* 42(1): 56-61 (2004)—Abstract.

Pharmaceutical and Food Safety Bureau, Ministry of Health, Labour and Welfare, "Report on Deliberation Results," (2008).

Ammar et al., Novel Pirfenidone Analogues: Synthesis of Pyridin-2-Ones for the Treatment of Pulmonary Fibrosis. *Arch Pharm* 339(8):429-36 (2006).

Raghu et al., Treatment of Idiopathic Pulmonary Fibrosis With a New Antifibrotic Agent, Pirfenidone: Results of a Prospective, Open-Label Phase Ii Study. *Am J Respir Crit Care Med* 159(4-Pt 1):1061-1069 (1999).

Kakugawa et al., Pirfenidone attenuates expression of HSP47 in murine bleomycin-induced pulmonary fibrosis. *Eur Respir J* 24(1):57-65 (2004).

Kaibori et al., Pirfenidone Protects Endotoxin-Induced Liver Injury After Hepatic Ischemia in Rats. *Transplantation Proceedings* 36(7):1973-1974 (2004).

Kaibori et al., Effects of Pirfenidone on Endotoxin-Induced Liver Injury After Partial Hepatectomy in Rats. *Transplantation Proceedings* 36(7):1975-1976 (2004).

Gagnon, L. Drug Slows Loss of Lung Capacity in Patients with Idiopathic Pulmonary Fibrosis. *Medscape Medical News* (2008).

Abboud, et al. Drug-Induced Liver Injury. *Drug Safety* 30(4):277-294 (2007).

Jain et al., Clinical Consideration of Drug-Induced Hepatotoxicity. *University of Southern California*, Los Angeles CA Elsevier (2010).

Tajiri et al., Practical guidelines for diagnosis and early management of drug-induced liver injury. *World J Gastroenterol* 14(44):6774-6785 (2008).

US Department of Health and Human Services, "Guidance for Industry-Drug Induced Liver Injury: Premarketing Clinical Evaluation," (2009).

Seymour, "Division Memorandum of Feb. 12, 2010."

Karimi-Shah, "Pirfenidone Capsules NDA 22-535, S-000," Pulmonary-Allergy Drugs Advisory Committee Meeting, US Food and Drug Administration (2010).

Porter, Pirfenidone NDA 22-535, Pulmonary-Allergy Drugs Advisory Committee Meeting, US Food and Drug Administration (2010).

Annex I—Summary of Product Characteristics Esbriet 267 mg hard capsules, Intermune Europe Ltd. 1-12 (2011).

Aloxi® (palonosetron) package insert, Rev. Feb. 2008.

Antoniu, Pirfenidone for the treatment of idiopathic pulmonary fibrosis. *Expert Opinion on Investigational Drugs* 15: 823-828 (2006).

BuSpar® (buspirone HCl, USP) package insert.

Clozaril® (clozapine) package insert.

Correspondence received from FDA, NDA 22535.

Dolophine Hydrochloride (methadone hydrochloride) package insert.

European search report from EP 10250379.4 dated May 17, 2010.

Food and Drug Administration Center for Drug Evaluation and Research, Pulmonary-Allergy Drugs Advisory Committee (PADAC) Meeting Transcript (Tuesday, Mar. 9, 2010), available at http://www.fda.gov/downloads/AdvisoryCommittees/CommitteesMeetingMaterials/Drugs/Pulmonary-AllergyDrugsAdvisoryCommittee/UCM208806.pdf.

Fuhr et al., Inhibitory effect of grapefruit juice and its bitter principal, naringenin, on CYP1A2 dependent metabolism of caffeine in man, Br. J. Clin. Pharmac. 35:431-6 (1993).

He et al., Inactivation of cytochrome P45 3A4 by Bergamottin, a component of grapefruit juice, Chem. Res. Toxicol. 11:252-9 (1998).

Hemeryck et al., Selective serotonin reuptake inhibitors and cytochrome P-450 mediated drug-drug interactions: An update, Current Drug Metabolism 3:13-37 (2002).

(56) References Cited

OTHER PUBLICATIONS

Horn et al. Get to Know and Enzyme: CYP1A2, available at http://www.pharmacytimes.com/publications/issue/2007/2007-11/2007-11-8279 (2007).
Inderal® (propranolol hydrochloride, long-acting capsules) package insert.
Inderal® (propranolol hydrochloride capsule, extended release) package insert.
InterMune, Pirfendione Briefing Document (Publication date Mar. 9, 2010).
International Search Report and Written Opinion of related case PCT/US10/058943.
Jeppesen et al., Dose-dependent inhibition of CYP1A2, CYP2C19 and CYP2D6 by citalopram, fluoxetine, fluovaxamine and paroxetine, European Journal of Clinical Pharmacology, 41 (1):73-78 (1996).
Landi et al., Human cytochrome P4501A2, IARC Scientific Publications 148:173-195 (1999).
Lexotan (bromazepam) package insert.
Malarone® (atovaquone and proguanil hydrochloride) package insert.
Mexitil® (mexiletine hydrochloride, USP) package insert.
Naropin® (ropivacaine hydrochloride monohydrate) package insert.
Odansetron product information from the UK Medicines and Healthcare Products Regulatory Agency.
Pirfenex®, Pirfenidone tablets 200 mg, package insert, Mar. 2011.
Quinidine Gluconate package insert.
Remington's: the Science and Practice of Pharmacy, Nineteenth Edition, 1:806.
Scriabine et al., New developments in the therapy of pulmonary fibrosis, Advances in Pharmacology 57:419-464 (2009).
Shionogi & Co., Ltd., Pirespa Tablet Report on the Deliberation Results, Evaluation and Licensing Division, Pharmaceutical and Food Safety Bureau, Ministry of Health, Labour and Welfare (Sep. 16, 2008).
Taniguchi et al., Pirfenidone in idiopathic pulmonary fibrosis, Eur. Respir. J. 35:821-829 (2010).
Thioridazine Hydrochloride package insert.
Tofranil (imipramine hydrochloride) package insert.
Zofran® (odansetron) package insert Apr. 2002.
Zyprexa® (olanzapine) package insert, Rev. Jan. 27, 2010.
Temple, Hy's law: predicting serious hepatotoxicity, Pharmacoepidemiology and Drug Safety 15:241-243 (2006).
Papay et al., Positive Rechallenge Following Drug-induced Liver Cases, Transcript of Presentation (Mar. 2008).

\* cited by examiner

PIRFENIDONE TREATMENT FOR PATIENTS WITH ATYPICAL LIVER FUNCTION

CROSS-REFERENCE TO RELATED APPLICATIONS

This is the national phase of International Application No. PCT/US2009/063702, filed Nov. 9, 2009, which claims priority to U.S. Provisional Application Nos. 61/113,107, filed Nov. 10, 2008, and 61/228,943, filed Jul. 27, 2009, and is a continuation of U.S. patent application Ser. No. 12/553,292, filed Sep. 3, 2009 (now U.S. Pat. No. 7,635,707 granted Dec. 22, 2009), which claims priority to U.S. Provisional Application No. 61/228,943, filed Jul. 27, 2009, and is a continuation-in part of U.S. patent application Ser. No. 12/488,228, filed Jun. 19, 2009, now abandoned, which is a continuation of U.S. patent application Ser. No. 12/428,393, filed Apr. 22, 2009 (now U.S. Pat. No. 7,566,729, granted Jul. 28, 2009), which claims priority to U.S. Provisional Application Ser. No. 61/113,107, filed Nov. 10, 2008, the disclosures of which are incorporated by reference in their entirety.

BACKGROUND

1. Field of the Disclosure

The disclosure relates generally to methods for reducing adverse effects associated with the treatment of diseases and disorders. More particularly, the disclosure relates to methods for reducing abnormal liver function associated with 5-methyl-1-phenyl-2-(1H)-pyridone ("pirfenidone") therapy.

2. Brief Description of Related Technology

U.S. Pat. Nos. 3,974,281, 4,042,699, and 4,052,509 generally relate to pirfenidone administration. U.S. Pat. Nos. 5,310,562, 5,518,729, and 5,716,632, all to Margolin and incorporated by reference herein, relate to pirfenidone administration.

Pulmonary fibrosis can be caused by a number of different conditions, including sarcoidosis, hypersensitivity pneumonitis, collagen vascular disease, and inhalant exposure. Idiopathic pulmonary fibrosis (IPF) is a distinct entity, characterized by breathing difficulty, radiographic abnormalities, and progressive loss of lung function. It is invariably progressive, and carries a grave prognosis with a median life expectancy of 2-3 years.

Pirfenidone has been administered to IPF patients. In a compassionate-use study, Raghu et al. ("Treatment of idiopathic pulmonary fibrosis with a new antifibrotic agent, pirfenidone: results of a prospective, open-label phase II study." Am J Respir Crit Care Med 159:1061-1069, 1999) reported administration of pirfenidone. No adverse events in hematology or blood chemistry were noted.

Nagai et al. conducted an uncontrolled, open-label study of pirfenidone in patients ("Open label compassionate use one year-treatment with pirfenidone to patients with chronic pulmonary fibrosis." Internal Medicine 41:1118-1123, 2002). During treatment, no liver dysfunctions, hematologic abnormalities, or allergic or shock reactions were reported.

Moises et al. "A double-blind, multicenter study comparing pirfenidone and prednisone for moderate-to-severe pulmonary fibrosis." Chest 124:116S, 2003 reported administration of pirfenidone.

Azuma et al. "Double-blind, placebo-controlled trial of pirfenidone in patients with idiopathic pulmonary fibrosis." Am J Respir Crit Care Med 171:1040-1047, 2005) describes administration of pirfenidone to a maximum of 1800 mg/day of pirfenidone, and reports a protocol for stepwise reduction and rechallenge with drug after an adverse event.

Abnormal liver function may manifest as abnormalities in levels of biomarkers of liver function, including alanine transaminase, aspartate transaminase, bilirubin, and/or alkaline phosphatase, and may be an indicator of drug-induced liver injury. See *FDA Draft Guidance for Industry. Drug-Induced Liver Injury: Premarketing Clinical Evaluation*, October 2007.

SUMMARY

One aspect of the invention provides methods for administering a therapeutically effective dose of pirfenidone to a patient that has exhibited abnormal biomarkers of liver function after pirfenidone administration for the treatment of fibrosis, e.g. idiopathic pulmonary fibrosis (IPF). In some embodiments, a patient is identified who exhibits a significantly abnormal level of one, two, three or more biomarkers of liver function, e.g. the level of a Grade 2 abnormality, after administration of an original full target dose of pirfenidone, e.g. about 2400 mg/day or 2403 mg/day. In such patients, the dose of pirfenidone is reduced or discontinued until levels of the abnormal biomarkers approach or are within normal range, after which patients are administered increasing doses of pirfenidone, up to the original full target dose. Alternatively, the dose of pirfenidone is not reduced at all, but liver biomarkers continue to be monitored. In another embodiment, after an optional temporary dose reduction or discontinuation, patients are administered pirfenidone at a permanently reduced dose of 1602 mg/day. As used herein, "original full target dose" means the therapeutically effective dose approved by the U.S. Food and Drug Administration or a similar agency in a foreign country, optionally other than Japan. In some embodiments, the original full target dose is about 2400 mg/day or 2403 mg/day pirfenidone, or about 34 mg/kg/day (e.g. 33-35 mg/kg/day), or from 2200 to 2600 mg/day pirfenidone, or from 31 mg/kg/day to 37 mg/kg/day. The total daily dose is administered one, two or three times per day.

Thus, the invention provides methods of administering pirfenidone to a patient at doses of 2400 mg/day or 2403 mg/day after identifying that the patient has exhibited a liver function Grade 2 abnormality after pirfenidone administration. In some embodiments, the methods involve continuing the full target dose, e.g. of 2400 mg/day or 2403 mg/day, without temporarily discontinuing or reducing the dose. The patient's biomarkers of liver function may continue to be monitored. In some embodiments, the method involves (a) administering a dose lower than 2400 mg/day for a time period, e.g., one week, two weeks, three weeks, four weeks, one month, six weeks, or two months, followed by (b) administering a dose of 2400 mg/day or 2403 mg/day. In specific embodiments, the pirfenidone is temporarily discontinued before step (a).

In some embodiments of the methods, pirfenidone is administered to a patient exhibiting a liver function Grade 2 abnormality as follows: (a) administering about 1600 mg/day or 1602 mg/day pirfenidone for about one week, or until the liver function biomarkers return to Grade 0 or Grade 1, and (b) administering the original full target dose for at least one week, two weeks, three weeks, four weeks or a month, two months, or three months, or one year, or two years, or three years, or four years, or five years, or seven years, or ten years. Preferably, the total daily dose is administered three times per day, with food.

In some embodiments of the methods, pirfenidone is administered to a patient exhibiting a liver function Grade 2 abnormality as follows: (a) administering about 800 mg/day or 801 mg/day pirfenidone for about one week, or until the liver function biomarkers return to Grade 0 or Grade 1, (b) administering about 1600 mg/day or 1602 mg/day pirfenidone for about one week, and (c) administering the original full target dose for a time period of at least one week, two weeks, three weeks, four weeks or a month, two months, or three months, or one year, or two years, or three years, or four years, or five years, or seven years, or ten years. Preferably, the total daily dose is administered three times per day, with food.

In some embodiments of the methods, pirfenidone is administered to a patient exhibiting a liver function Grade 2 abnormality as follows: (a) discontinuing pirfenidone for about one week, or until the liver function biomarkers return to Grade 0 or Grade 1, (b) administering about 800 mg/day or 801 mg/day pirfenidone for about one week, (c) administering about 1600 mg/day or 1602 mg/day pirfenidone for about one week, and (d) administering the original full target dose for a time period of at least one week, two weeks, three weeks, four weeks or a month, two months, or three months, or one year, or two years, or three years, or four years, or five years, or seven years, or ten years. Preferably, the total daily dose is administered three times per day, with food.

Alternatively, pirfenidone is administered to a patient exhibiting a liver function Grade 2 abnormality at a permanently reduced dose, e.g. 800 or 801 mg/day, or 1600 or 1602 mg/day. In some embodiments, pirfenidone is administered to a patient exhibiting a liver function Grade 2 abnormality as follows: administering about 1600 mg/day or 1602 mg/day pirfenidone for a time period of at least one week, two weeks, three weeks, four weeks or a month, two months, or three months, or one year, or two years, or three years, or four years, or five years, or seven years, or ten years. In some embodiments, pirfenidone is administered to a patient exhibiting a liver function Grade 2 abnormality as follows: (a) administering about 800 mg/day or 801 mg/day pirfenidone for about a week, or until biomarkers of liver function are within normal limits, and (b) administering about 1600 mg/day or 1602 mg/day pirfenidone to the patient for a time period of at least one week, two weeks, three weeks, four weeks or a month, two months, or three months, or one year, or two years, or three years, or four years, or five years, or seven years, or ten years.

In other embodiments, pirfenidone is administered to a patient exhibiting a liver function Grade 2 abnormality as follows: (a) discontinuing pirfenidone for about one week, or until the liver function biomarkers return to Grade 0 or Grade 1, (b) administering about 800 mg/day or 801 mg/day pirfenidone for about a week, or until biomarkers of liver function are within normal limits, and (c) administering about 1600 mg/day or 1602 mg/day pirfenidone to the patient for a time period of at least one week, two weeks, three weeks, four weeks or a month, two months, or three months, or one year, or two years, or three years, or four years, or five years, or seven years, or ten years. In still other embodiments, pirfenidone is administered to a patient exhibiting a liver function Grade 2 abnormality as follows: (a) discontinuing pirfenidone for about one week, or until the liver function biomarkers return to Grade 0 or Grade 1, and (b) administering about 1600 mg/day or 1602 mg/day pirfenidone to the patient for a time period of at least one week, two weeks, three weeks, four weeks or a month, two months, or three months, or one year, or two years, or three years, or four years, or five years, or seven years, or ten years.

The invention also provides methods of administering pirfenidone to a patient at doses of 2400 mg/day or 2403 mg/day after identifying that the patient has exhibited a liver function Grade 1 abnormality after pirfenidone administration. In some embodiments, the methods involve continuing the full target dose, e.g. of 2400 mg/day or 2403 mg/day, without temporarily discontinuing or reducing the dose. The patient's biomarkers of liver function may continue to be monitored. In some embodiments, the method involves (a) administering a dose lower than 2400 mg/day for a time period, e.g., one week, two weeks, three weeks, four weeks, one month, six weeks, or two months, followed by (b) administering a dose of 2400 mg/day or 2403 mg/day. In specific embodiments, the pirfenidone is temporarily discontinued before step (a).

In some embodiments of the methods, pirfenidone is administered to a patient exhibiting a liver function Grade 1 abnormality as follows: (a) administering about 1600 mg/day or 1602 mg/day pirfenidone for a time period, optionally about one week, or until the liver function biomarkers return to Grade 0, and (b) administering the original full target dose for at least one week, two weeks, three weeks, four weeks or a month, two months, or three months, or one year, or two years, or three years, or four years, or five years, or seven years, or ten years. Preferably, the total daily dose is administered three times per day, with food.

In some embodiments of the methods, pirfenidone is administered to a patient exhibiting a liver function Grade 1 abnormality as follows: (a) administering about 800 mg/day or 801 mg/day pirfenidone for a time period, optionally about one week, or until the liver function biomarkers return to Grade 0, (b) administering about 1600 mg/day or 1602 mg/day pirfenidone for a time period, optionally about one week, and (c) administering the original full target dose for a time period of at least one week, two weeks, three weeks, four weeks or a month, two months, or three months, or one year, or two years, or three years, or four years, or five years, or seven years, or ten years. Preferably, the total daily dose is administered three times per day, with food.

In some embodiments of the methods, pirfenidone is administered to a patient exhibiting a liver function Grade 1 abnormality as follows: (a) discontinuing pirfenidone for a time period, optionally about one week, or until the liver function biomarkers return to Grade 0, (b) administering about 800 mg/day or 801 mg/day pirfenidone for a time period, optionally about one week, (c) administering about 1600 mg/day or 1602 mg/day pirfenidone for a time period, optionally about one week, and (d) administering the original full target dose for a time period of at least one week, two weeks, three weeks, four weeks or a month, two months, or three months, or one year, or two years, or three years, or four years, or five years, or seven years, or ten years. Preferably, the total daily dose is administered three times per day, with food.

Alternatively, pirfenidone is administered at a permanently reduced dose, e.g. 800 or 801 mg/day, or 1600 or 1602 mg/day. In some embodiments, pirfenidone is administered to a patient exhibiting a liver function Grade 1 abnormality as follows: administering about 1600 mg/day or 1602 mg/day pirfenidone for a time period of at least one week, two weeks, three weeks, four weeks or a month, two months, or three months, or one year, or two years, or three years, or four years, or five years, or seven years, or ten years. In some embodiments, pirfenidone is administered to a patient exhibiting a liver function Grade 1 abnormality as follows: (a) administering about 800 mg/day or 801 mg/day pirfenidone for a time period, optionally about a week, or until biomarkers of liver function are within normal limits, and (b) administering about 1600 mg/day or 1602 mg/day pirfenidone to the patient for a time period of at least one week, two weeks, three weeks, four weeks or a month, two months, or three months, or one year, or two years, or three years, or four years, or five years, or seven years, or ten years.

In other embodiments, pirfenidone is administered to a patient exhibiting a liver function Grade 1 abnormality as follows: (a) discontinuing pirfenidone for a time period, optionally about one week, or until the liver function biomarkers return to Grade 0, (b) administering about 800 mg/day or 801 mg/day pirfenidone for about a week, or until biomarkers of liver function are within normal limits, and (c) administering about 1600 mg/day or 1602 mg/day pirfenidone to the patient for a time period of at least one week, two weeks, three weeks, four weeks or a month, two months, or three months, or one year, or two years, or three years, or four years, or five years, or seven years, or ten years. In still other embodiments, pirfenidone is administered to a patient exhibiting a liver function Grade 1 abnormality as follows: (a) discontinuing pirfenidone for a time period, optionally about one week, or until the liver function biomarkers return to Grade 0, and (b) administering about 1600 mg/day or 1602 mg/day pirfenidone to the patient for a time period of at least one week, two weeks, three weeks, four weeks or a month, two months, or three months, or one year, or two years, or three years, or four years, or five years, or seven years, or ten years.

In any of the embodiments described herein, any of the reduced doses of pirfenidone may be administered for a time period of 2 days, 3 days, 4 days, 5 days, 6 days, one week, about two weeks, or until the level of at least one biomarker of liver function has returned to within normal limits, or until all biomarkers or liver function has returned to within normal limits.

In any of the embodiments described herein, the patient can have fibrotic lesional tissue. Such a patient is a patient who would benefit from pirfenidone administration. In one embodiment, the patient is suffering from pulmonary fibrosis, idiopathic interstitial pneumonia, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, and/or skin lesions. In one embodiment, the patient is suffering from lymph node fibrosis associated with HIV. In one embodiment, the patient is suffering from pulmonary fibrosis, or idiopathic pulmonary fibrosis. In another embodiment, the patient is a person who would benefit from pirfenidone administration, optionally with the proviso that the patient is not suffering from idiopathic pulmonary fibrosis.

In some embodiments, the biomarker of liver function is alanine transaminase, aspartate transaminase, bilirubin, and/or alkaline phosphatase. Elevated gamma-glutamyl transferase has been observed in some patients receiving pirfenidone, without clinical liver impairment, and thus elevated gamma-glutamyl transferase alone is not necessarily a sign of liver impairment. In any of the embodiments described herein, biomarkers of liver function can exclude gamma-glutamyl transferase. In another embodiment, the abnormal level of alanine transaminase, aspartate transaminase, or alkaline phosphatase is greater than about 2.5-fold increased compared to the upper limit of normal (ULN). In a related embodiment, the abnormal level of alanine transaminase, aspartate transaminase, or alkaline phosphatase is greater than about 2.5- to about 5-fold increased compared to the upper limit of normal (ULN), i.e. a "liver function Grade 2 abnormality". In some embodiments, the abnormal level of bilirubin is greater than about 1.5- to about 3-fold increased compared to the upper limit of normal (ULN), i.e., a "liver function Grade 2 abnormality".

In some embodiments the abnormal biomarkers of liver function, e.g. elevated alanine transaminase and/or aspartate transaminase and/or elevated bilirubin, are accompanied by clinical signs of impaired liver function such as jaundice.

Further aspects and advantages will be apparent to those of ordinary skill in the art from a review of the following detailed description, taken in conjunction with the examples. While the method is susceptible of embodiments in various forms, the description hereafter includes specific embodiments with the understanding that the disclosure is illustrative, and is not intended to limit the invention to the specific embodiments described herein.

DETAILED DESCRIPTION

The invention provides methods for administering a full therapeutically effective dose of pirfenidone to a patient that has exhibited abnormal levels of biomarkers of liver function after the patient has been treated with pirfenidone. Because liver function abnormalities can be indicative of drug-induced liver injury (hepatotoxicity), it is important to determine whether the abnormalities reflect liver injury or merely indicate limited toxicity that will resolve over time while continuing to take the drug. According to the present invention, even patients that exhibit abnormal liver function may continue taking pirfenidone at the original full target dose, optionally after a short time period of discontinuing pirfenidone or taking the pirfenidone at reduced doses. This administration regimen has the advantage of maximizing the time on the full target dose of drug and therefore the potential for a beneficial therapeutic effect.

The patient may be suffering from any disease for which pirfenidone therapy may be useful in ameliorating symptoms. Such a patient is a patient who would benefit from pirfenidone administration. These diseases include, but are not limited to: chronic obstructive pulmonary disease (COPD), inflammatory pulmonary fibrosis (IPF), rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis, irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as Multiple Sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation; protozoal diseases.

The methods of the invention optionally include identifying abnormal liver function in a patient receiving pirfenidone, and monitoring biomarkers of liver function in a patient receiving a reduced dose of pirfenidone. In any of the methods described herein, AST and/or ALT may be elevated, e.g. to a Grade 2 or Grade 3 level. In some embodiments, the elevation is to a Grade 1 level. Alternatively, AST and bilirubin may be elevated, or AST or ALP may be elevated, or AST and GGT may be elevated, or ALT and bilirubin may be elevated, or ALT and ALP may be elevated, or ALT and GGT may be elevated, or bilirubin and ALP may be elevated, or bilirubin and GGT may be elevated, e.g., to a Grade 1, Grade 2, or Grade 3 level. Alternatively, three biomarkers of liver function may be elevated, e.g., ALT and AST and bilirubin, or ALT and AST and ALP, to a Grade 1, Grade 2, or Grade 3 level. In any of the embodiments described herein, biomarkers of liver function can exclude gamma-glutamyl transferase.

In some embodiments of the methods, pirfenidone is administered to a patient exhibiting a liver function Grade 2 abnormality after pirfenidone administration as follows: (a) administering at least about 1600 mg/day or 1602 mg/day pirfenidone, or about 23 mg/kg/day (e.g. 22-24 mg/kg/day), or from 1400-1800 mg/day pirfenidone, or from 20 mg/kg/day to 26 mg/kg/day, for a time period. In some embodiments, step (a) is followed by (b) administering the original full target dose. In other embodiments, the original full target dose is continued without a temporary reduction or discontinuation of the dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or until all biomarkers or liver function has returned to within normal limits. In some embodiments, step (b) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b).

In some embodiments of the methods, pirfenidone is administered to a patient exhibiting a liver function Grade 2 abnormality as follows: (a) administering at least about 800 mg/day or 801 mg/day pirfenidone, or about 11 mg/kg/day (e.g. 10-12 mg/kg/day), or from 600-1000 mg/day, or from 700-900 mg/day, or from 8 mg/kg/day to 15 mg/kg/day, for a time period, (b) administering at least about 1600 mg/day or 1602 mg/day pirfenidone, or about 23 mg/kg/day (e.g. 22-24 mg/kg/day), or from 1400-1800 mg/day pirfenidone, or from 20 mg/kg/day to 26 mg/kg/day, for a time period, and (c) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (c) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c).

In some embodiments of the methods, pirfenidone is administered to a patient exhibiting a liver function Grade 2 abnormality as follows: (a) discontinuing pirfenidone for a time period, (b) administering at least about 800 mg/day or 801 mg/day pirfenidone, or about 11 mg/kg/day (e.g. 10-12 mg/kg/day), or from 600-1000 mg/day, or from 700-900 mg/day, or from 8 mg/kg/day to 15 mg/kg/day, for a time period, (c) administering at least about 1600 mg/day or 1602 mg/day pirfenidone, or about 23 mg/kg/day (e.g. 22-24 mg/kg/day), or from 1400-1800 mg/day pirfenidone, or from 20 mg/kg/day to 26 mg/kg/day, for a time period, and (d) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (c) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (d) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c) and/or step (d).

In some embodiments of the methods, pirfenidone is administered to a patient exhibiting a liver function Grade 1 abnormality as follows: (a) administering at least about 1600 mg/day or 1602 mg/day pirfenidone, or about 23 mg/kg/day (e.g. 22-24 mg/kg/day), or from 1400-1800 mg/day pirfenidone, or from 20 mg/kg/day to 26 mg/kg/day, for a time period, and (b) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or until all biomarkers or liver function has returned to within normal limits. In some embodiments, step (b) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b).

In some embodiments of the methods, pirfenidone is administered to a patient exhibiting a liver function Grade 1 abnormality as follows: (a) administering at least about 800 mg/day or 801 mg/day pirfenidone, or about 11 mg/kg/day (e.g. 10-12 mg/kg/day), or from 600-1000 mg/day, or from 700-900 mg/day, or from 8 mg/kg/day to 15 mg/kg/day, for a time period, (b) administering at least about 1600 mg/day or 1602 mg/day pirfenidone, or about 23 mg/kg/day (e.g. 22-24 mg/kg/day), or from 1400-1800 mg/day pirfenidone, or from 20 mg/kg/day to 26 mg/kg/day, for a time period, and (c) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (c) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c).

In some embodiments of the methods, pirfenidone is administered to a patient exhibiting a liver function Grade 1 abnormality as follows: (a) discontinuing pirfenidone for a time period, (b) administering at least about 800 mg/day or 801 mg/day pirfenidone, or about 11 mg/kg/day (e.g. 10-12 mg/kg/day), or from 600-1000 mg/day, or from 700-900 mg/day, or from 8 mg/kg/day to 15 mg/kg/day, for a time period, (c) administering at least about 1600 mg/day or 1602 mg/day pirfenidone, or about 23 mg/kg/day (e.g. 22-24 mg/kg/day), or from 1400-1800 mg/day pirfenidone, or from 20 mg/kg/day to 26 mg/kg/day, for a time period, and (d) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (c) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (d) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c) and/or step (d).

Pirfenidone can be provided in tablet or capsule forms or any other oral dosage form, and typically is formulated for oral administration. Exemplary capsule formulations are described in WO 2007/038315 (Int'l Appl. No. PCT/US2006/037057).

Pirfenidone therapy can be associated with adverse effects including photosensitivity rash, anorexia (decreased appetite), stomach discomfort, nausea, heartburn, drowsiness (somnolence), fatigue, upper respiratory tract infection, fever, positive urinary occult blood, elevation of C-reactive protein (CRP), decreased weight, headache, constipation, and malaise. Abnormal liver function also can occur as an adverse effect (AE) in patients receiving pirfenidone. Prior to receiving pirfenidone, the baseline liver function of the patient can be, and typically is, normal. Liver function can be assessed by various means known in the art, such as blood chemistry tests measuring biomarkers of liver function. Examples of biomarkers of liver function include, but are not limited to, alanine transaminase (ALT), aspartate transaminase (AST), bilirubin, alkaline phosphatase (ALP), and gamma-glutamyl transferase (GGT).

Alanine transaminase (ALT), also called serum glutamic pyruvate transaminase (SGPT) or alanine aminotransferase (ALAT), catalyzes the transfer of an amino group from alanine to α-ketoglutarate to produce pyruvate and glutamate. When the liver is damaged, levels of ALT in the blood can rise due to the leaking of ALT into the blood from damaged or necrosed hepatocytes.

Aspartate transaminase (AST) also called serum glutamic oxaloacetic transaminase (SGOT or GOT) or aspartate aminotransferase (ASAT), catalyzes the transfer of an amino group from aspartate to α-ketoglutarate to produce oxaloacetate and glutamate. AST can increase in response to liver damage. Elevated AST also can result from damage to other sources, including red blood cells, cardiac muscle, skeletal muscle, kidney tissue, and brain tissue. The ratio of AST to ALT can be used as a biomarker of liver damage.

Bilirubin is a catabolite of heme that is cleared from the body by the liver. Conjugation of bilirubin to glucuronic acid by hepatocytes produces direct bilirubin, a water-soluble product that is readily cleared from the body. Indirect bilirubin is unconjugated, and the sum of direct and indirect bilirubin constitutes total bilirubin. Elevated total bilirubin can be indicative of liver impairment.

Alkaline phosphatase (ALP) hydrolyzes phosphate groups from various molecules and is present in the cells lining the biliary ducts of the liver. ALP levels in plasma can rise in response to liver damage, and are higher in growing children and elderly patients with Paget's disease. However, elevated ALP levels usually reflect biliary tree disease.

Adverse effect Grades for abnormal liver function are defined herein by the modified Common Toxicity Criteria (CTC) provided in Table 1. See the Common Terminology Criteria for Adverse Events v3.0 (CTCAE) published Aug. 9, 2006 by the National Cancer Institute, incorporated herein by reference in its entirety.

TABLE 1

Modified Common Toxicity Criteria

| Toxicity | Grade | | | | |
|---|---|---|---|---|---|
| | 0 | 1 | 2 | 3 | 4 |
| ALT | WNL | >ULN-2.5 × ULN | >2.5-5 × ULN | >5-20 × ULN | >20 × ULN |
| AST | WNL | >ULN-2.5 × ULN | >2.5-5 × ULN | >5-20 × ULN | >20 × ULN |
| Bilirubin | WNL | >ULN-1.5 × ULN | >1.5-3 × ULN | >3-10 × ULN | >10 × ULN |
| ALP | WNL | >ULN-2.5 × ULN | >2.5-5 × ULN | >5-20 × ULN | >20 × ULN |
| GGT | WNL | >ULN-2.5 × ULN | >2.5-5 × ULN | >5-20 × ULN | >20 × ULN |

(WNL = within normal limits; ULN = upper limit of normal)

The ULN for various indicators of liver function depends on the assay used, the patient population, and each laboratory's normal range of values for the specified biomarker, but can readily be determined by the skilled practitioner. Exemplary values for normal ranges for a healthy adult population are set forth in Table 2 below. See Cecil Textbook of Medicine, pp. 2317-2341, W.B. Saunders & Co. (1985).

TABLE 2

| ALT | 8-20 U/L |
| AST | 8-20 U/L |
| Bilirubin | 0.2-1.0 mg/dL |
| | 3.4-17.1 µmol/L |
| ALP | 20-70 U/L |
| GGT | Men: 9-50 U/L |
| | Women: 8-40 U/L |

Grade 0 levels are characterized by biomarker levels within normal limits (WNL). "Normal" liver function, as used herein, refers to Grade 0 adverse effects. "Abnormal" liver function, as used herein, refers to Grade 1 and above adverse effects.

"Grade 1 liver function abnormalities" include elevations in ALT, AST, ALP, or GGT greater than the ULN and less than or equal to 2.5-times the ULN. Grade 1 liver function abnormalities also include elevations of bilirubin levels greater than the ULN and less than or equal to 1.5-times the ULN.

"Grade 2 liver function abnormalities" include elevations in alanine transaminase (ALT), aspartate transaminase (AST), alkaline phosphatase (ALP), or gamma-glutamyl transferase (GGT) greater than 2.5-times and less than or equal to 5-times the upper limit of normal (ULN). Grade 2 liver function abnormalities also include elevations of bilirubin levels greater than 1.5-times and less than or equal to 3-times the ULN.

"Grade 3 liver function abnormalities" include elevations in ALT, AST, ALP, or GGT greater than 5-times and less than or equal to 20-times the ULN. Grade 3 liver function abnormalities also include elevations of bilirubin levels greater than 3-times and less than or equal to 10-times the ULN.

"Grade 4 liver function abnormalities" include elevations in ALT, AST, ALP, or GGT greater than 20-times the ULN. Grade 4 liver function abnormalities also include elevations of bilirubin levels greater than 10 the ULN.

The present disclosure provides methods for treating a patient having idiopathic pulmonary fibrosis and receiving a full target dose of pirfenidone, wherein the full target dose is 2400 or 2403 mg pirfenidone per day. In accordance with the methods, a patient with abnormal liver function is administered a second dose of pirfenidone, wherein the second dose is 1600 or 1602 mg pirfenidone per day until liver function is within normal limits, followed by administering the patient the full target dose of 2400 or 2403 mg pirfenidone per day.

The present disclosure also provides methods for treatment of patients that exhibit Grade 1 abnormality in one or more biomarkers of liver function after pirfenidone administration. The method includes administering to the patient pirfenidone at doses of 2400 mg/day or 2403 mg/day or administering to the patient pirfenidone at doses of 1600 mg/day or 1602 mg/day. Preferably, the patient may be receiving pirfenidone for treatment of idiopathic pulmonary fibrosis. Alternatively, the patient may be suffering from a condition for which pirfenidone administration may be beneficial. Optionally, patients may receive reduced doses or discontinue treatment for a time period, and then resume administration of pirfenidone.

The methods disclosed herein are contemplated to include embodiments including any combination of one or more of the additional optional elements, features, and steps further described herein (including those described in the examples), unless stated otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

It will be appreciated that the invention provides pirfenidone as a medicament wherein the administration pattern of the medicament comprises administering according to any of the treatment methods described herein.

It will be appreciated that the invention provides pirfenidone for use in treating a patient with idiopathic pulmonary fibrosis or a patient who would benefit from pirfenidone administration according to any of the treatment regimes as described above with respect to the methods of the invention for administering pirfenidone to a patient for treating idiopathic pulmonary fibrosis or to a patient who would benefit from pirfenidone administration. Pirfenidone is packaged and presented for use in a treating a patient with idiopathic pulmonary fibrosis or a patient who would benefit from pirfenidone administration according to such treatment regimes. Pirfenidone is administered to the patient in accordance with the treatment regimes as described above. The patient is one who has exhibited abnormal biomarkers of liver function after pirfenidone administration as is described above with respect to the methods of the invention for administering pirfenidone to a patient for treating idiopathic pulmonary fibrosis or to a patient who would benefit from pirfenidone administration.

In particular, the invention includes pirfenidone for use in treating a patient with idiopathic pulmonary fibrosis or a patient who would benefit from pirfenidone administration, said patient having exhibited a Grade 1 or Grade 2 abnormality in one or more biomarkers of liver function after pirfenidone administration, wherein said patient is administered pirfenidone at doses of 2400 mg/day or 2403 mg/day. Optionally, prior to administration of pirfenidone at doses of 2400 mg/day or 2403 mg/day, said patient is administered pirfenidone at doses lower than 2400 mg/day for a time period.

It will be appreciated that the invention provides the use of pirfenidone in the manufacture of a medicament for treating a patient with idiopathic pulmonary fibrosis or a patient who would benefit from pirfenidone administration according to any of the treatment regimes as described above with respect to any of the methods. The medicaments manufactured according to this aspect of the invention are for use in treating a patient with idiopathic pulmonary fibrosis or a patient who would benefit from pirfenidone administration in accordance with such treatment regimes. The medicament so manufactured is administered to the patient in accordance with the treatment regimes as described above. The patient is one who has exhibited abnormal biomarkers of liver function after pirfenidone administration as is described above with respect to the methods of the invention for administering pirfenidone to a patient for treating idiopathic pulmonary fibrosis or a patient who would benefit from pirfenidone administration.

In particular, the invention includes the use of pirfenidone in the manufacture of a medicament for treating a patient with idiopathic pulmonary fibrosis or a patient who would benefit from pirfenidone administration, said patient having exhibited a Grade 1 or Grade 2 abnormality in one or more biomarkers of liver function after pirfenidone administration, wherein said patient is administered pirfenidone at doses of 2400 mg/day or 2403 mg/day. Optionally, prior to administration of pirfenidone at doses of 2400 mg/day or 2403 mg/day, said patient is administered pirfenidone at doses lower than 2400 mg/day for a time period.

In respect of the aspects of the invention relating to pirfenidone for use in treating a patient with idiopathic pulmonary fibrosis, and to use of pirfenidone in the manufacture of a medicament for treating a patient with idiopathic pulmonary fibrosis, the preferences expressed with respect to the preferred embodiments of the aspect of the invention relating to a method for administering pirfenidone to treat a patient with idiopathic pulmonary fibrosis apply in the same way. Similarly, the examples relate to pirfenidone for use in treating a patient with idiopathic pulmonary fibrosis, and to use of pirfenidone in the manufacture of a medicament for treating a patient with idiopathic pulmonary fibrosis, as well as to a method for administering pirfenidone to a patient for treating idiopathic pulmonary fibrosis.

EXAMPLES

The following examples are provided for illustration and are not intended to limit the scope of the invention.

Example 1

Pirfenidone Dosing Regimen

Patients begin pirfenidone treatment by receiving escalating doses of pirfenidone over a period of 15 days until the full maintenance dose is reached. Specifically, from days 1 to 7, patients are administered one capsule of 267 mg pirfenidone three times per day. During days 8 to 14, patients receive two capsules of 267 mg pirfenidone three times per day. From day 15 onward, patients are treated with three capsules of 267 mg pirfenidone three times per day. Pirfenidone is administered orally, and each dose should be taken with food. If the patient is unable to eat, then the pirfenidone dose should be taken with milk or juice (excluding grapefruit juice).

Pirfenidone is known to cause photosensitivity reactions; therefore, throughout the treatment period, patients should use sun block that protects against at least UV-A with a sun protective factor (SPF) of 50. In addition, patients should wear appropriate clothing to minimize sun exposure, and if possible, avoid other medications known to cause photosensitivity reactions.

Once the full maintenance dose is reached, pirfenidone is administered orally to patients three times per day to provide a daily dose of 2403 mg pirfenidone. Each of the three doses of 801 mg pirfenidone includes three capsules of 267 mg pirfenidone each. The contents of the pirfenidone 267 mg capsules are pirfenidone (82.15%); croscarmellose sodium (8.15%); microcrystalline cellulose (7.39%); povidine, USP, EP (1.85%); and magnesium stearate (0.46%).

Patients are treated with pirfenidone for up to 72 weeks. Some patients are treated longer than 72 weeks. At weeks 2, 4, 6, 12, and every 12 weeks (±2 weeks) thereafter during the treatment period, with the exception of week 72 and the treatment completion visit, patients are examined and histories are collected as detailed in the steps below.

1. Patient history is collected to include review of adverse effects (AEs) and severe adverse effects (SAEs), use of concomitant medications, use of oxygen, hospitalizations, IPF exacerbations or acute respiratory decompensation, and dosing.

2. Patients receive a physical examination, and vital signs and weight are measured.

3. Pulmonary function is assessed by spirometry before and after administration of bronchodilators. Forced vital capacity (FVC) and forced expiratory volume in 1 second (FEV1) are measured.

4. Clinical laboratory tests are performed, including hematology, serum chemistries, pregnancy tests for women of childbearing capacity, and urinalysis with microscopic examination.

5. Questionnaires are administered, including the University of California at San Diego Shortness of Breath Questionnaire (UCSD SOBQ), St. George's Hospital Respiratory Questionnaire (SGRQ), and the World Health Organization Quality of Life (WHO QOL) questionnaire. After week 72, only the UCSD SOBQ and SGRQ are obtained at the scheduled 12 week visits.

Additionally, every 24 weeks starting with Week 12 (for example, weeks 12, 36, and 60), electrocardiogram (ECG) measurements are obtained. ECG data is obtained before administering bronchodilators for the pulmonary function test (PFT) measurements. At the week 36 visit, pharmacokinetic (PK) data is obtained for selected patients.

If a patient experiences a Grade 1 or greater elevation in alanine transaminase (ALT), aspartate transaminase (AST), or bilirubin at baseline or after the start of pirfenidone dosing up to and including week 6, an additional safety chemistry blood test must be obtained between weeks 8 and 10.

Example 2

Modification of Pirfenidone Dosing Regimen in Response to Grade 2 Liver Function Test (LFT) Elevations Patients are treated with pirfenidone in accordance with Example 1. During the course of pirfenidone treatment, patients exhibiting abnormal liver function test results are candidates for dose modification. As described in Example 1, serum chemistry tests are performed at scheduled intervals during the treatment period to monitor various parameters, including biomarkers of liver function such as alanine transaminase (ALT), aspartate transaminase (AST), bilirubin, alkaline phosphatase (ALP), and gamma-glutamyl transferase (GGT).

If a patient experiences a Grade 2 increase in any one of AST, ALT or bilirubin, the pirfenidone dose is reduced to one capsule of 267 mg pirfenidone three times per day. While receiving the reduced pirfenidone dose, the patient undergoes additional monitoring of AST, ALT and bilirubin. The reduced pirfenidone dose is continued at least until AST, ALT and bilirubin are all Grade 1 or within normal limits (Grade 0). The reduced pirfenidone dose can be administered for a period of time after AST, ALT and bilirubin have reached Grade 1 or Grade 0.

At any time after AST, ALT and bilirubin have resolved to Grade 0 or Grade 1, the pirfenidone dose can be re-escalated in a manner consistent with the initial dose escalation, up to a dose of 6 capsules per day. After AST, ALT and bilirubin have resolved to Grade 0 or Grade 1, the pirfenidone dose also can be re-escalated in a manner consistent with the initial dose escalation, up to the maximum of 9 capsules per day.

Serum chemistry tests are optionally performed at scheduled intervals during the escalation period, e.g. weekly or every 2 weeks, or every 3 weeks, or every month to monitor various parameters, including biomarkers of liver function such as alanine transaminase (ALT), aspartate transaminase (AST), bilirubin, alkaline phosphatase (ALP), and gamma-glutamyl transferase (GGT).

Example 3

Temporary Discontinuation of Pirfenidone Dosing in Response to Grade 2 Liver Function Test (LFT) Elevations Patients are treated with pirfenidone in accordance with Example 1. During the course of pirfenidone treatment, patients exhibiting abnormal liver function test results are candidates for dose modification. As described in Example 1, serum chemistry tests are performed at scheduled intervals during the treatment period to monitor various parameters, including biomarkers of liver function such as alanine transaminase (ALT), aspartate transaminase (AST), bilirubin, alkaline phosphatase (ALP), and gamma-glutamyl transferase (GGT).

If a patient experiences a Grade 2 increase in any one of AST, ALT or bilirubin, the pirfenidone dose is discontinued. Following discontinuation of the pirfenidone dose, the patient undergoes additional monitoring of AST, ALT and bilirubin. Pirfenidone dosing is discontinued at least until AST, ALT and bilirubin are all Grade 1 or within normal limits (Grade 0). The pirfenidone dose can be discontinued for a period of time after AST, ALT and bilirubin have reached Grade 1 or Grade 0.

After AST, ALT and bilirubin have resolved to Grade 0 or Grade 1, if the patient has been off drug for 14 days or more, the pirfenidone dose is re-escalated in a manner consistent with the initial dose escalation, up to a dose of 6 or 9 capsules per day, i.e. 1602 mg/day or 2403 mg/day. Alternatively, after AST, ALT and bilirubin have resolved to Grade 0 or Grade 1, the pirfenidone dose is re-instituted at a dose of 6 capsules per day, i.e. 1602 mg/day, and re-escalated after 1 week to the maximum of 9 capsules per day.

Serum chemistry tests are optionally performed at scheduled intervals during the escalation period, e.g. weekly, or every 2 weeks, or every month, to monitor various parameters, including biomarkers of liver function such as alanine transaminase (ALT), aspartate transaminase (AST), bilirubin, alkaline phosphatase (ALP), and gamma-glutamyl transferase (GGT).

Example 4

Modification of Pirfenidone Dosing Regimen to 2 Capsules Three Times per Day in Response to Grade 2 Liver Function Test (LFT) Elevations Patients are treated with pirfenidone in accordance with Example 1. During the course of pirfenidone treatment, patients exhibiting abnormal liver function test results are candidates for dose modification. As described in Example 1, serum chemistry tests are performed at scheduled intervals during the treatment period to monitor various parameters, including biomarkers of liver function such as alanine transaminase (ALT), aspartate transaminase (AST), bilirubin, alkaline phosphatase (ALP), and gamma-glutamyl transferase (GGT).

If a patient experiences a Grade 2 increase in any one of AST, ALT or bilirubin, the pirfenidone dose is reduced to two capsules of 267 mg pirfenidone three times per day, i.e. 1602 mg/day. While receiving the reduced pirfenidone dose, the patient undergoes additional monitoring of AST, ALT and bilirubin. The reduced pirfenidone dose is continued at least until AST, ALT and bilirubin are all Grade 1 or within normal limits (Grade 0). The reduced pirfenidone dose can be administered for a period of time after AST, ALT and bilirubin have reached Grade 1 or Grade 0.

After 1 week of treatment at 1602 mg/day, if AST, ALT and bilirubin have resolved to Grade 0 or Grade 1, the pirfenidone dose can be re-escalated to the maximum of 9 capsules per day, i.e. 2403 mg.

Example 5

No Modification of Pirfenidone Dosing Regime in Response to a Grade 1 or Grade 2 Liver Function Test (LFT) Elevations Patients were treated with pirfenidone in accordance with Example 1. During the course of pirfenidone treatment, some patients exhibited abnormal liver function test results. As described in Example 1, serum chemistry tests were performed at scheduled intervals during the treatment period to monitor various parameters, including biomarkers of liver function such as alanine transaminase (ALT), aspartate transaminase (AST), bilirubin, alkaline phosphate (ALP), and gamma-glutamyl transferase (GGT).

If a patient exhibited a Grade 1 or Grade 2 increase in any one of AST, ALT, or bilirubin, the pirfenidone dose was not reduced for some patients. The patient continued to receive the full target dose of 2403 mg/day. While receiving the full target dose, the patient was monitored for AST, ALT, and bilirubin levels.

Example 6

Incidence of Liver Function Abnormality and Dosing Regimen Response

Grade 1 Abnormalities in Liver Function

In a study of 345 patients with idiopathic pulmonary fibrosis receiving pirfenidone three times per day for a total daily dose of 2403 mg/day, 49 patients without a baseline liver function abnormality exhibited a Grade 1 elevation in AST or ALT levels after pirfenidone administration. Of the 49 patients, three patients with a Grade 1 liver function test elevation had a treatment emergent adverse event of increased AST or ALT. In one patient, study drug dose was reduced to 1602 mg/day for the remainder of study participation (from Day 51 to Day 602), and the Grade 1 AST or ALT abnormality returned to Grade 0. For the second patient, study drug dose was reduced to 1602 mg/day and then increased to 2403 mg/day for remainder of study participation, and ALT returned to Grade 0. The third patient had study drug dose reduced to 801 mg/day, ultimately completing study at 1602 mg/day, at which time ALT returned to Grade 0. The remaining patients (46 patients) received no dose modification.

Grade 2 Abnormalities in Liver Function

Fifteen patients developed a Grade 2 liver function test abnormality in AST and/or ALT levels after pirfenidone administration of 2403 mg/day. Of the fifteen patients, 12 had reported treatment emergent adverse events of increased AST or ALT or hepatitis. The liver function test elevations for the remaining three patients were not documented as an adverse event (discussed below).

Of the twelve patients, two patients received continued administration of pirfenidone at the full daily dose of 2403 mg/day. The liver function test of one patient resolved to a Grade 0. The other patient had a history of steatosis and a Grade 1 abnormality prior to pirfenidone treatment and underwent a dose reduction for unrelated reasons (rash and diarrhea), not for abnormal liver function tests, and ended the study with a Grade 1 elevation.

Two patients had a temporary dose reduction or a temporary discontinuation of pirfenidone, and were rechallenged and escalated back to full dose. They completed the study at the full dose of 2403 mg/day with normal liver enzymes.

Seven patients underwent a permanent dose reduction of pirfenidone, in some cases after a temporary discontinuation of drug; by completion of the study, 3 patients were receiving 801 mg/day and 4 patients were receiving 1602 mg/day. With the exception of one patient, rechallenge with a higher dose was not attempted with these patients. The patient that was rechallenged received the full dose of 2403 mg/day, but the dose was later reduced due to a recurrence of Grade 2 elevation in ALT levels. All seven patients completed the study with resolution of transaminases, except for one patient that had a Grade 1 elevation at study completion.

One patient discontinued treatment due to abnormal liver function tests in AST and/or ALT levels. The dose for this patient was initially decreased to 1602 mg/day, then discontinued, and then resumed at 1602 mg/day. For this patient, however, treatment was permanently discontinued because a Grade 2 elevation of AST coincided with a Grade 3 ALT elevation in liver function tests.

Of the three patients whose liver function test elevations were not documented as an adverse event, one had Grade 1 AST and ALT elevation at baseline, and experienced a Grade 1 elevation of AST at the last documented assessment. This patient received no dose modification after a Grade 2 elevation in AST and/or ALT levels. A second patient with a Grade 2 transaminase elevation had treatment temporarily discontinued for acute cerebral artery occlusion. Transaminase levels returned to normal once the dose was escalated back to 2403 mg/day, and the patient completed the study on full dose with normal transaminases. The third patient had no liver function test abnormalities while on treatment until Day 422, then the patient experienced a Grade 2 AST and Grade 1 ALT elevation with respiratory failure due to IPF. Study drug was discontinued the same day for respiratory failure. The patient was hospitalized on Day 434 and died on Day 439 due to respiratory failure.

Grade 3 Abnormalities in Liver Function

Four patients developed Grade 3 liver function abnormality in AST and/or ALT levels after pirfenidone administration, all of who had a treatment emergent adverse event of either increased AST and/or ALT. Two of the four patients discontinued study drug for elevated liver function tests. In both instances, the abnormalities had not resolved, with Grade 2 and Grade 3 abnormalities last documented. The two other patients had Grade 1 abnormalities at screening and/or baseline. One patient discontinued for lung transplant at which time the last documented values showed a Grade 1 abnormality. The other patient interrupted study drug (investigator decision), and subsequently discontinued study drug (sponsor decision). The AST and ALT elevations had normalized at the last documented value.

The foregoing description is given for clearness of understanding only, and no unnecessary limitations should be understood therefrom, as modifications within the scope of the invention may be apparent to those having ordinary skill in the art. Although methods have been described with reference to particular embodiments, a person of ordinary skill in the art will readily appreciate that other ways of performing the acts associated with the methods may be used.

All patents, publications and references cited herein are hereby fully incorporated by reference. In case of conflict between the present disclosure and incorporated patents, publications and references, the present disclosure should control.

What is claimed is:

1. A method of treating a patient in need of pirfenidone and suffering from a Grade 2 abnormality in a liver function biomarker selected from the group consisting of alanine transaminase (ALT) and aspartate transaminase (AST) and wherein the abnormality occurs after a first pirfenidone administration, comprising providing to said patient a second administration of pirfenidone, comprising (a) administering to said patient at doses of at least 1600 mg/day or 1602 mg/day.

2. The method of claim 1 comprising (a) administering to said patient pirfenidone at doses of 2400 mg/day or 2403 mg/day.

3. The method of claim 2 wherein the second administration of pirfenidone further comprises, prior to step (a), administering to said patient pirfenidone at doses lower than 2400 mg/day.

4. The method of claim 1 further comprising, prior to step (a), discontinuing the first administration pirfenidone for about one week, or until biomarkers of liver function are within normal limits.

5. The method of claim 2 wherein the second administration further comprises, prior to step (a), administering about 1600 mg/day or 1602 mg/day pirfenidone for about one week, or until biomarkers of liver function are within normal limits.

6. The method of claim 2 wherein the second administration further comprises, prior to step (a), administering about 800 mg/day or 801 mg/day pirfenidone for about one week, or until biomarkers of liver function are within normal limits, followed by administering about 1600 mg/day or 1602 mg/day pirfenidone for about one week, or until biomarkers of liver function are within normal limits.

7. The method of claim 2 further comprising, prior to step (a), discontinuing the first administration of pirfenidone for about one week, or until biomarkers of liver function are within normal limits.

8. The method of claim 1, wherein the pirfenidone is administered three times per day with food.

9. The method of claim 1 further comprising the step of measuring one or more of AST and ALT.

10. The method according to claim 1, wherein the second administration of pirfenidone further comprises, prior to step (a), administering to said patient pirfenidone at doses lower than 1600 mg/day.

11. The method according to claim 10, wherein the second administration of pirfenidone further comprises, prior to step (a), discontinuation of pirfenidone administration to the patient for about one week or until biomarkers of liver function are within normal limits.

12. The method according to claim 1, wherein the second administration of pirfenidone further comprises, prior to step (a), about 800 mg/day or 801 mg/day to the patient for about one week, or until biomarkers of liver function are within normal limits.

13. The method according to claim 10, wherein the pirfenidone is administered three times per day with food.

14. The method according to claim 10 further comprising measuring one or more of ALT and AST during administration of pirfenidone.

15. The method of claim 2 wherein the second administration further comprises, prior to step (a), administering about 800 mg/day or 801 mg/day pirfenidone for about one week, or until biomarkers of liver function are within normal limits, followed by administering about 1600 mg/day or 1602 mg/day pirfenidone for about one week, or until biomarkers of liver function are within normal limits.

16. The method of claim 1, wherein step (a) comprises administering to said patient pirfenidone at a dose of about 1800 mg/day.

17. The method of claim 1, wherein the patient suffers from fibrosis.

18. The method of claim 1, wherein the patient suffers from a condition selected from the group consisting of renal fibrosis, vascular fibrosis and scleroderma.

19. The method of claim 1, wherein the patient suffers from idiopathic pulmonary fibrosis.

* * * * *